United States Patent [19]

Pirt

[11] Patent Number: 5,540,839
[45] Date of Patent: Jul. 30, 1996

[54] PROCESS FOR DEGRADING ORGANIC MATTER

[75] Inventor: Stanley J. Pirt, London, United Kingdom

[73] Assignee: Pirtferm Limited, London, United Kingdom

[21] Appl. No.: 204,141

[22] PCT Filed: Aug. 27, 1992

[86] PCT No.: PCT/EP92/02000

§ 371 Date: Feb. 28, 1994

§ 102(e) Date: Feb. 28, 1994

[87] PCT Pub. No.: WO93/04988

PCT Pub. Date: Mar. 18, 1993

[30] Foreign Application Priority Data

Aug. 30, 1991 [GB] United Kingdom .................. 9118560

[51] Int. Cl.⁶ .................................................. C02F 3/12
[52] U.S. Cl. ........................ 210/612; 210/624; 210/626; 210/605
[58] Field of Search .................... 210/605, 612, 210/613, 623, 624, 626, 630

[56] References Cited

U.S. PATENT DOCUMENTS

| | | | |
|---|---|---|---|
| 3,926,794 | 12/1975 | Vahldieck | 210/673 |
| 3,964,998 | 6/1976 | Barnard | 210/605 |
| 3,994,802 | 11/1976 | Casey et al. | 210/605 |
| 4,198,211 | 4/1980 | Shattock | 210/612 |
| 4,246,099 | 1/1981 | Gould et al. | 210/673 |
| 4,582,607 | 4/1986 | Kiese et al. | 210/612 |
| 4,655,925 | 4/1987 | Tabata et al. | 210/605 |
| 4,915,840 | 4/1990 | Rozich | 210/613 |
| 5,192,442 | 3/1993 | Piccirillo et al. | 210/605 |

FOREIGN PATENT DOCUMENTS

| | | |
|---|---|---|
| 78919 | 5/1983 | European Pat. Off. . |
| 3615971 | 11/1987 | Germany . |
| 3622750 | 1/1988 | Germany . |
| 2105318 | 3/1983 | United Kingdom . |
| WO92/01779 | 2/1992 | WIPO . |
| WO93/22418 | 11/1993 | WIPO . |

OTHER PUBLICATIONS

New York Sewage Works (Journal WPCF, vol. 57, No. 2, pp. 116–121).

*Primary Examiner*—Christopher Upton
*Attorney, Agent, or Firm*—Pennie & Edmonds

[57] ABSTRACT

A cyclical process for degrading waste organic matter to gaseous products and substantially zero volume of solid matter by subjecting the waste alternately and cyclically to stages of mesophilic and thermophilic digestion in which the organisms from one stage are inactivated and become a substrate for the organisms in the next stage, this inactivation resulting from a temperature shift. At the end of the cycle, solids are collected and returned to the first microbial digestion stage for recycling together with a fresh input of waste.

18 Claims, 4 Drawing Sheets

PROCESS FOR DEGRADING ORGANIC MATTER

The present invention relates to a process for degrading organic matter and in particular to a process for degradation of sewage into gaseous products.

Microbiological degradation, either aerobic or anaerobic, is the preferred means to purify waste organic matter, for example sewage or effluents from industry. A major drawback of this technology is the production of 'sludge' which is a suspension of solid material, probably for the most part, microbial biomass which degrades the organic matter and, in the process, grows in quantity. The yield of sludge volatile suspended solids (VSS) can exceed 0.4 kg per kg chemical oxygen demand (COD) under aerobic conditions and up to a half of that amount under anaerobic conditions. Sludge is routinely disposed of by dumping on land or at sea. Now, because of the adverse environmental effects dumping the sludge is increasingly banned. Hence there is an urgent need for new technology for sludge disposal.

We have now developed a cyclical degradation process comprising low temperature (mesophilic) and high temperature (thermophilic) steps wherein the resulting suspended solids resulting from each stage are susceptible to digestion in, and form a metabolic substrate for, the following stage when the two process steps are operated alternately and cyclically whereby it is possible to degrade the organic matter completely to gaseous products and thereby avoid the production of solid effluent.

A New York sewage works (Journal WPCF, Vol. 57, No. 2, pages 116–121) has proposed a sewage disposal system in which two chemostats are connected in series, one being run under thermophilic conditions and the other under mesophilic conditions, a part of the solid effluent being recycled. There was no suggestion, however, that it would be possible to achieve total biocombustion and a large part of the solid effluent had to be disposed of at sea.

Similarly U.S. Pat. No. 4,582,607 describes a similar system which is advocated for producing activated sludge in a form capable of efficient sedimentation and, again, there is no suggestion that the biomass could be totally degraded.

According to the present invention, we provide a method of degradation of organic matter, wherein said organic matter in aqueous suspension and/or solution is subjected alternately and cyclically to mesophilic and thermophilic digestion, whereby in the mesophilic stage said organic matter and any thermophilic microorganisms present are at least partly digested and whereby in said thermophilic stage said organic matter and any mesophilic microorganisms present are at least partly digested, and whereby said cyclic treatment is continued until the organic material is substantially completely converted into gaseous degradation products.

In this way, organic matter may be subject to total degradation and volatilization by such an alternating cycle of microbial digestion stages which we have called a "biocycle". This total elimination of organic material from the sludge results in reduction to mineral residues only.

The thermophilic and mesophilic stages operate at temperatures appropriate for the respective microbial populations, the lower temperature mesophilic stage operating at a temperature between 10°–50° C., preferably 30°–40° C. and more preferably 37° C. with the higher, thermophilic stage operating at within the range 40°–105° C., preferably 70°–90° C., more preferably 80° C. Thus in cycling between the two stages, the material is subjected to a temperature shift which is sufficient to inactivate the organisms from the preceding stage. Typically this shift will be in the range of 20°–70° C., preferably 40° C., this being at least in part determined by other operating conditions including, for example, ambient temperature, and pasteurisation time for pathogens in the first stage.

The two digestion processes may conveniently be carried out in fermentor vessels and it is desirable that the suspended cells remain in constant contact with the medium to avoid settling out. Typical vessels suitable for such a purpose are those described in our co-pending International Patent Application, No. PCT/EP91/01323 filed on 12 Jul. 1991, the contents of which are included herein by reference, in which a central vertical panel divides the main fermentor tank and a gas flow causes the medium moving longitudinally along the vessel length also to move cyclically in a direction perpendicular to this flow. Such vessels may conveniently be provided separately or in parallel or series combination in order to be scaled up whilst maintaining optimal reaction conditions for the digestion steps. Other typical vessels which may be suitable are described in our copending British Patent Application No. 9209175.0 filed 28 Apr. 1992, the contents of which are included herein by reference, in which vessels of the type described above are additionally provided with transverse baffles.

The thermophilic stage is typically operated in an aerobic fashion; however, the mesophilic stage may be operated in either an aerobic or an anaerobic mode. In the aerobic mode, the organic matter is degraded to carbon dioxide; such a process is termed 'biocombustion'. Operation in the anaerobic mode permits methanogenic degradation. The anaerobic mode is particularly applicable when the waste organic matter is highly concentrated, for example animal manure and agricultural crop residues.

The organisms of the aerobic mesophilic population are typically gram-negative and gram-positive rod-shaped bacteria of the type characteristic of the activated sludge process for sewage purification, for example Acinetobacter and Brevibacterium species, and the inoculum may conveniently be obtained from a conventional sewage purification plant. The anaerobic mesophilic population typically comprises gram-positive and gram-negative bacteria, and may include facultative anaerobes which serve to eliminate traces of oxygen, and methane producers, for example Methanothrix. The organisms of the thermophilic population are predominantly small gram-positive rod-shaped bacteria, including, for example, Bacillus species. The inoculum for the thermophilic stage may be developed, for example, by culturing organisms from a composted manure heap.

According to a further aspect of the present invention, we provide an apparatus for degrading organic matter in stages comprising an assembly wherein the outlet means of one or more first-stage tanks are connected to the inlet means of one or more second-stage tanks while the outlet means of said second-stage tank(s) are connected to the inlet means of the first-stage tank(s), each of said tanks being provided additionally with means for recycling liquid from its outlet to its inlet and with means for independently controlling the temperature therein.

In the simplest assembly a single first tank is connected to a single second tank in the manner described. However, it is possible for a number of first tanks to be connected in parallel to one or more second tanks, or vice versa, to allow for the possibility of processing different volumes of liquid in the two stages. It is also possible for the system to operate in a multistage process wherein the outflow from a second stage may be at least partially returned either the original first stage tank from which the material entered the second stage (when only two tanks are used), or further first stage and second stage tanks (where more than two tanks are used), optionally with return of material to the initial tank to repeat the cycle.

The process may operate conveniently as a four-stage process, with two thermophilic and two mesophilic stages operating alternately, preferably carried out in separate vessels.

The process may also be carried out in a single vessel in which the temperature and other conditions are changed successively and, if necessary, an inoculum of fresh organisms appropriate to each temperature stage added accordingly when the temperature is varied. In such a case, following completion of the desired number of stages, the culture is allowed to settle, with liquid being withdrawn out of the system and solids being retained for the next cycle with fresh waste for degradation.

It will be appreciated that in all embodiments of the system according to the invention, fresh inoculum will be added at the beginning of each fermentation stage, for example, by recycling partially digested sludge or adding inoculum from separate inoculum cultivation vessels.

In cases where it is desirable to remove the water, the outflow from the final vessel may pass to a sedimentation device, for example, a settler, to concentrate the final suspended solids consisting of active biomass and clarify the liquor. The cycle is completed by return of the sedimented solids to the inlet of the first reactor vessel for digestion together with fresh substrate and the clarified liquor is withdrawn from the system.

This process is an environmentally acceptable biotechnology which achieves, in an aqueous medium, the equivalent of complete combustion of organic matter. In addition the high temperature of the thermophilic stage facilitates recovery of the chemical energy as heat.

The process may be carried out in either plug flow mode, with recycling of biomass, as a batch process, or as completely mixed (stirred tank or chemostat) continuous cultures. In general, plug flow or batch fermentations are preferred to chemostat-type fermentors although a cycle of four or more chemostats with alternate thermophilic and mesophilic stages may approach plug flow conditions.

BRIEF DESCRIPTION OF THE DRAWINGS

Schematic diagrams of degradation systems according to the present invention are illustrated in the accompanying FIGS. 1 to 8, in which.

DESCRIPTION OF THE PREFERRED EMBODIMENTS

Figure 1:
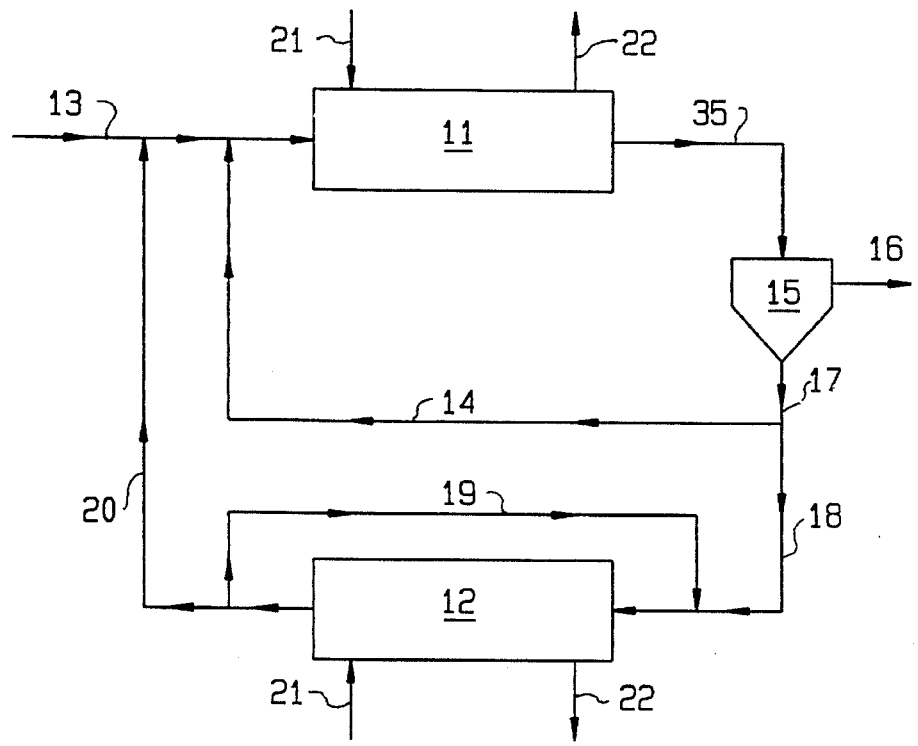
FIGS. 1 to 4 show a 2-stage system.

In a 2-stage system, the aerobic system shown in FIG. 1 consists of two degradation vessels or two sets of vessels, 11 and 12 operated in a cycle. These fermentors are preferably operated in the plug flow mode, although completely mixed continuous cultures (chemostat mode) may also be used. Sewage 13 is fed into the first stage 11 in which the aerobic digester is provided with an air or oxygen supply 21, and from which effluent gas emerges in stream 22. This is the mesophilic stage for which the preferred temperature is 23° C.; however the temperature may be in the range 15°–40° C. The mesophilic stage is operated on the activated sludge principle with feedback of a part of the separated sludge 14 to act as an inoculum and increase the biomass concentration. A separator 15 serves to concentrate the emerging sludge 35 and produce a clarified stream 16, which leaves the system, and a sludge stream 17, which is a concentrate of the suspended solids. The excess sludge 18 is fed to the aerobic, thermophilic stage 12 operated preferably at 80° C.; however, the possible range is about 60°–105° C. The thermophilic reactors are also equipped with air or oxygen supply 21 and effluent $CO_2$ emerges via stream 22. The thermophilic stage may conveniently maintain its temperature by self-heating. A part of the culture emerging from the thermophilic stage 19 is fed back to the inlet to act as an inoculum. The rest of the thermophilic culture 20 is returned to the mesophilic stage where the biomass of thermophilic origin is digested along with the sewage. The thermophilic culture 20 may be cooled prior to feeding into the mesophilic module. The rate of feed of the sludge into the thermophilic stage is limited by the maximum oxygen transfer rate in the fermentor. A working example showing the required feed rates of sewage and sludge and the oxygen transfer rates is given below.

A similar cycle of mesophilic and thermophilic stages may be used to oxidize biologically organic matter of sources other than sewage, for example, food industry wastes and agricultural and forestry crop residues, animal manures and municipal solid wastes and biodegradable plastic waste. If the wastes are in a concentrated form it is advantageous to feed them directly into the thermophilic stage and feed the mesophilic stage with thermophilic stage effluent.

Alternatively, for concentrated wastes, such as farm animal faecal wastes, the mesophilic, aerobic stage can be replaced by a mesophilic, anaerobic stage; which generates methane. A suitable degradation system is illustrated in FIG. 2, in which the methanogenic sludge, generated in digestor 29, is separated and degraded in the aerobic, thermophilic stage, the effluent from which is returned to the methanogenic stage which is maintained in the anaerobic mode.

Figure 2:
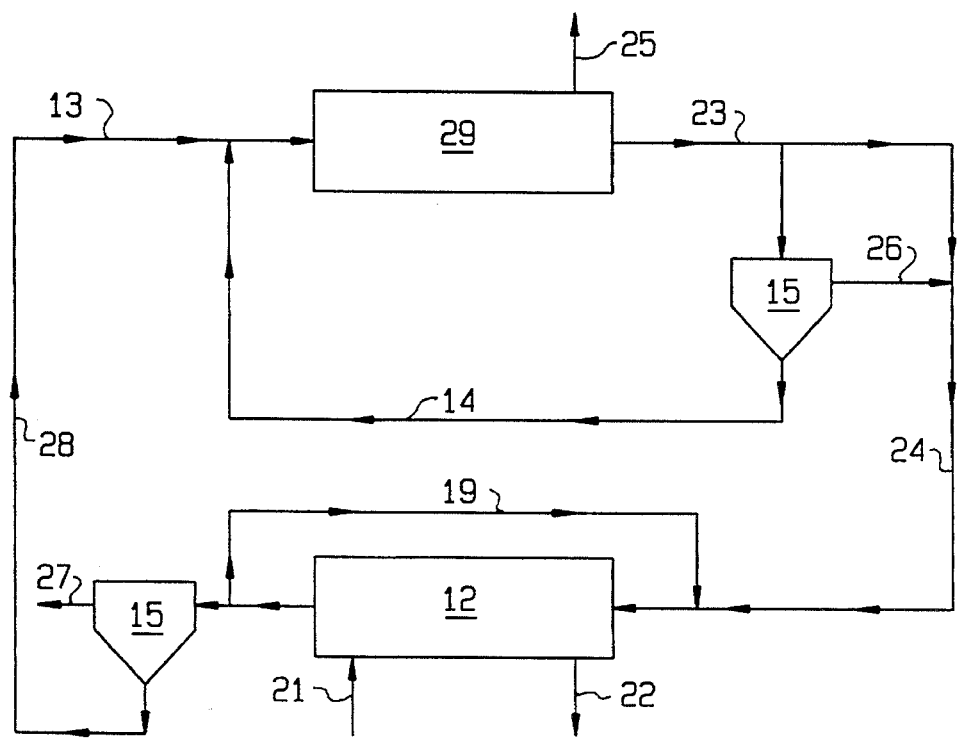

In FIG. 2, the mesophilic digestion vessel 29 is equipped with gas outlet stream 25 in which the methane produced emerges. A fraction of the liquid effluent 23 emerging from the mesophilic stage 29 is passed into a separator 15 to concentrate the solids in stream 14 which is fed back to the inlet of the mesophilic stage. The remainder of the effluent 23 combined with the supernatant liquid effluent 26 from the separator is passed via stream 24 to the thermophilic digestor 12. The liquor in effluent 23 from the mesophilic stage contains much dissolved organic matter, principally fatty acids which are removed by digestion in the thermophilic stage. Part of the effluent from the thermophilic digestor 12 is recycled in stream 19. The rest of the effluent from 12 passes into a further separator 15 from which issues the stream of concentrated solids 28 which is fed back to the mesophilic digestor.

The purified aqueous effluents recovered in streams 16 or 27 contain salts of the inorganic elements present in the sewage. If required, these elements, notably N, P and K can be recovered downstream.

In alternative embodiments of the process of the invention, the reaction conditions may be modified. In one such embodiment, a partial vacuum may be applied to the thermophilic digestor module to boil the aqueous media at a temperature below 100° C. and thus evaporate the liquid, concentrate the suspended solids and other dissolved substances and recover heat from the vapour. To achieve boiling the reduced pressure may conveniently be in the range 150 to 355 mmHg at 60° to 80° C., preferably at 355 mmHg at 80° C. In a second such embodiment, pressure may be applied to the thermophilic module to generate a superheated steam at temperatures up to about 105° C. when using microorganisms known to be active at such temperatures. Suitable pressures are conveniently in the range 760 to 906 mmHg, preferably 906 mmHg at 105° C.

Figure 3:
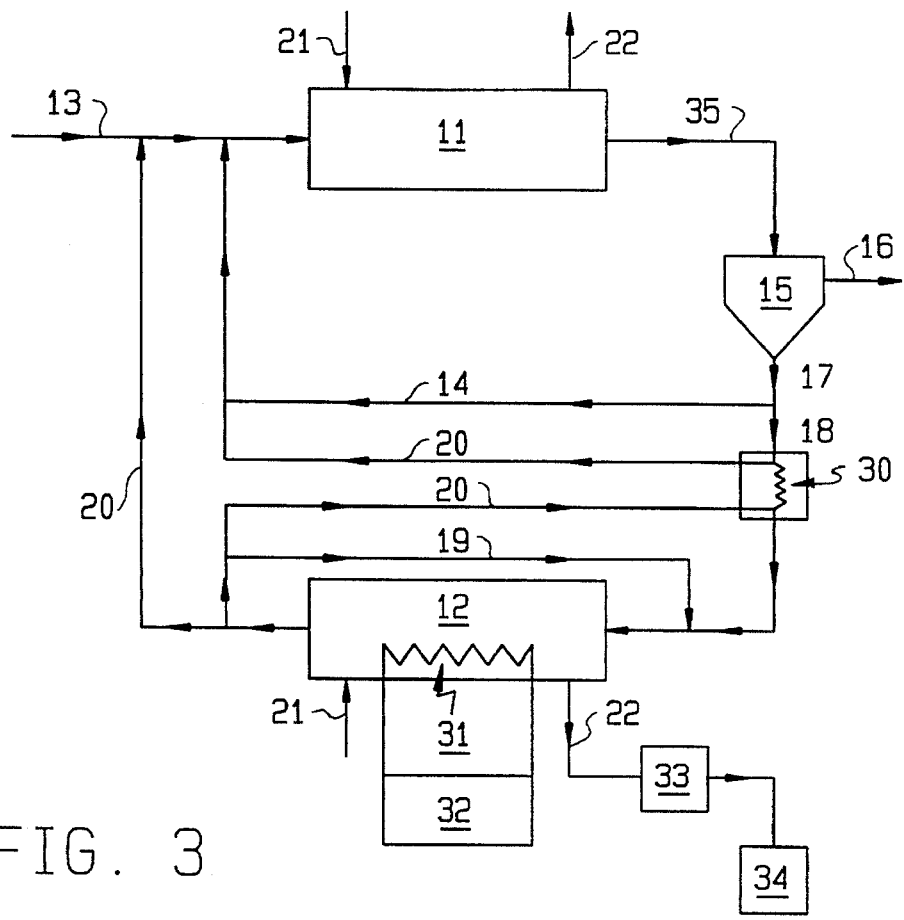

Two systems of temperature control of the thermophilic digestor are illustrated in FIG. 3. The heat exchanger 30 serves to transfer heat from the effluent thermophilic culture stream 20 to the influent stream 18. The heat exchanger 31 and the heat sink or source 32 serve to transfer heat to or from the thermophilic digestor.

Alternatively, the desired temperature in the reactor can be maintained by reducing the atmospheric pressure in the digestor until the contents reach boiling point, for example, 80° C. at 355 mmHg. The vacuum pump or blower 33 reduces the pressure in the digestor 12 and condenses the steam in the reservoir 34. In effect, this makes the thermophilic digestor equivalent to a combined combustion chamber and boiler.

The versatility of the system can be extended by the inclusion of additional stages in the cycle of fermenters, for example, anaerobic methanogenesis nitrification and denitrification stages. In order to favour the desired organisms and exclude competitors, some selective conditions, for example, of temperature, pH value, substrate or inhibitor should be applied in each stage.

Generalized Model of the Two Stage Aerobic Degradation

Figure 4:
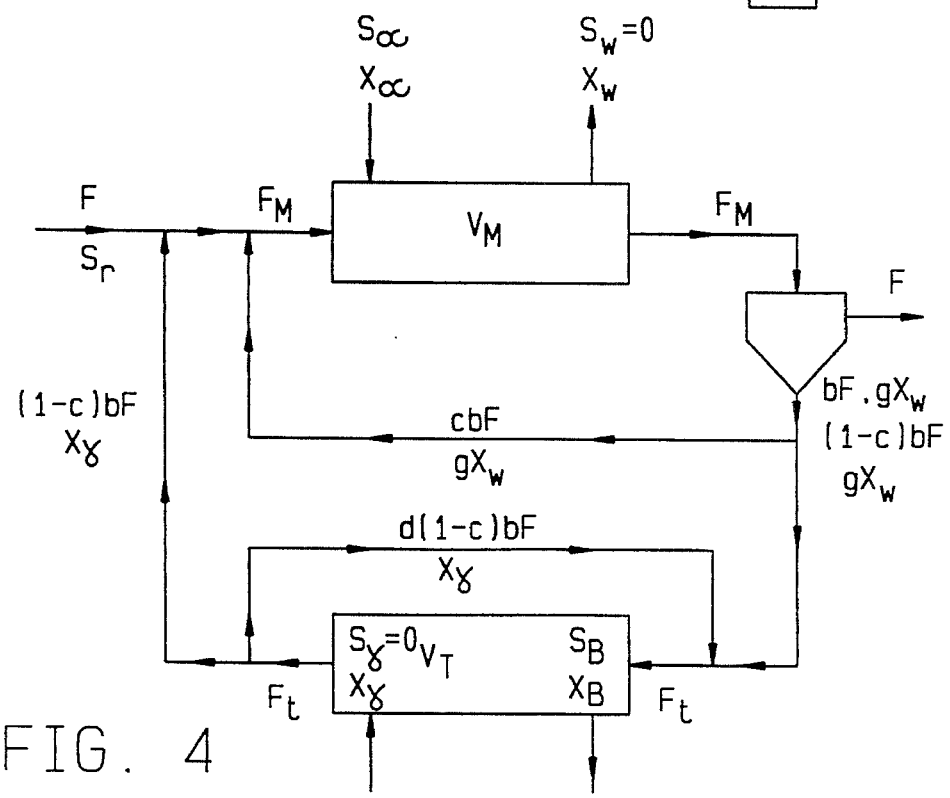

The generalized model of the process presented below enables the operator to accommodate his particular process requirements so as to achieve complete biological oxidation of the organic matter. The model is graphically represented in FIG. 4. The parameters of the particular example described below are derived from the model to illustrate its application.

Assumptions

The digestors act as plug flow systems in a steady state in which the conditions remain constant.

The organic substrate is aerobically metabolized with production of carbon dioxide and active biomass.

The concentration of the organic substrate fed into each digestor decreases linearly with distance along the digestor and becomes zero at the outlet of the digestor.

The biomass (sludge) formed in the mesophilic stage becomes the organic substrate in the thermophilic stage.

The thermophilic biomass fed into the mesophilic digestor becomes part of the organic substrate in the mesophilic stage.

Consumption of the organic substrate, irrespective of its nature or origin, results in growth of the active biomass with a yield of $Y_C$, kg dry biomass/kg organic substrate, and an oxygen consumption of $Y_{O/S}$ kgO$_2$/kg organic substrate.

Terms, Symbols and Units b=a fraction; of flow rate F in stream 17.
$B_o$=biochemical oxygen demand (B.O.D.) of stream 13, KgO$^2$m$^{-3}$
c=a fraction; of flow rate bF in stream 14.
d=a fraction; of recycled flow rate (1–c) bF in stream 19.
F=flow rate of sewage in stream 13, m$^3$h$^{-1}$.
$F_M$=liquid flow rate through mesophilic digestor, m$^3$h$^{-1}$
$F_T$=liquid flow rate through thermophilic digestor, m$^3$h$^{-1}$
g=biomass concentration factor achieved in separator 15
$H_M$=heat produced in mesophilic digestor, kJh$^{-1}$
$H_S$=surplus heat produced in thermophilic digestor, kJh$^{-1}$
$H_T$=heat produced in thermophilic digestor, kJh$^{-1}$
$H_{TD}$=heat required to raise temperature of water entering stream 18 from $T_M$ to $T_T$°C., kJh$^{-1}$ $r_{MD}$=oxygen demand in mesophilic digestor, KgO$_2$ m$^{-3}$h$^{-1}$
$r_T$=oxygen transfer rate in thermophilic digestor, kgO$_2$m$^{-3}$h$^{-1}$
$S_r$=concentration of organic substrate in sewage stream 13, kgm$^{-3}$
$S_\alpha$=concentration of organic matter at inlet of mesophilic digestor, kgm$^{-3}$
$S_\beta$=concentration of organic substrate at inlet of thermophilic digestor, kgm$^{-3}$
$S_\gamma$=concentration of organic substrate at outlet of thermophilic digestor kgm$^{-3}$
$S_\omega$=concentration of organic substrate at outlet of mesophilic digestor, kgm$^{-3}$
$t_{rM}$=residence time of liquid in mesophilic digestor ($V_M$/$F_M$), h
$t_{rT}$=residence time of liquid in thermophilic digestor ($V_T$/$F_T$), h
$T_M$=temperature in mesophilic digestor, °C.
$T_T$=temperature in thermophilic digestor, °C.
$x_\alpha$=active biomass concentration at the inlet of the mesophilic digestor, kg dry weight m$^{-3}$
$x_\beta$=active biomass concentration at the inlet of the thermophilic digestor, kg dry weight m$^{-3}$
$x_\gamma$=active biomass concentration at the outlet of the thermophilic digestor, kg dry weight m$^{-3}$
$x_\omega$=active biomass concentration at outlet of mesophilic digestor, kg dry weight m$^{-3}$
$V_M$=liquid content of mesophilic digestor, m$^3$
$V_T$=liquid content of thermophilic digestor, m$^3$
$Y_C$=yield of active biomass from the organic substrate, kg dry weight/kg substrate
$Y_{O/S}$=oxygen consumed/organic substrate consumed, kgO$_2$/kg organic substrate Mesophilic Stage $$x_\omega = x_\alpha + Y_c S_\alpha \quad (1)$$

$$F_M = (1+b)F \quad (2)$$

$$V_M = (1+b)F/t_{rM} \quad (3)$$

$$g = (1+b)/b \quad (4)$$

$$F_M x_\alpha = cbF \frac{(1+b)}{b} x_\omega$$

hence, $$x_\alpha = C x_\omega \quad (5)$$

$$F_M S_\alpha = FS_r + (1-c)bFx_\gamma$$

hence, $$S_\alpha = \frac{S_r + (1-c)bx_\gamma}{1+b} \quad (6)$$

$$S_r = B_o/Y_{o/s} \quad (6a)$$

From equations (6) and (19)

$$S_\alpha = \frac{S_r}{1+b} + (1-c)Y_c x_\omega \quad (7)$$

From equations (1), (5) and (7)

$$x_\omega = Y_c S_r / \{(1+b)(1-c)(1-Y_c^2)\} \quad (8)$$

From equation (8)

$$C = (A - Y_c S_r)/A \quad (9)$$

where $$A = (1+b)(1-Y_c^2)x_\omega$$

The oxygen demand in the mesophilic digestor is $$r_{MD} = Y_{o/s} S_\alpha F(1+b)/V_M \quad (10)$$

that is, $$r_{MD} = Y_{o/s} \frac{F}{V_m} \{S_r + (1-c)(1+b)Y_c x_\omega\} \quad (11)$$

Thermophilic Stage $$x_\gamma = x_\beta + Y_C S_\beta \quad (12)$$

$$t_{rT} = V_T/F_T$$

$$F_T x_\beta = d(1-c)bF x_\gamma \quad (13)$$

$$F_T = (1-c)bF + d(1-c)bF \quad (14)$$

hence, $$F_T = bF(1-c)(1+d) \quad (15)$$

$$x_\beta = dx_\gamma/(1+d) \quad (16)$$

$$F_T S_\beta = (1-c)bF \frac{(1+b)}{b} x_\omega \quad (17)$$

hence, $S_\beta = \frac{(1+b)x_\omega}{b(1+d)} \quad (18)$ and $x_\gamma = \frac{(1+b)}{b} Y_c x_\omega \quad (19)$ From equations (16) and (19), $$x_\beta = \frac{d(1+b)Y_c x_\omega}{b(1+d)} \quad (20)$$

The residence time required in the thermophilic stage ($t_{rT}$) is fixed by the oxygen transfer rate and the oxygen demand.

$$t_{rT} = Y_{o/s} S_\beta / r_T \quad (21)$$

hence, $$V_T = Y_{o/s} S_\beta F_T / r_T \quad (22)$$

From equations (15), (18) and (22)

$$V_T = F Y_{o/s} x_\omega (1-c)(1+b)/r_T \quad (23)$$

Heat Production

The heat production in the process is 460 kJ/mol $O_2$ consumed, that is, $14.38 \times 10^3$ kJ/kg$O_2$ The heat produced in the mesophilic digestor is $$H_M = 14.38 \times 10^3 r_{MD} V_M \quad (24)$$

The heat produced in the thermophilic digestor is $$H_T = 14.38 \times 10^3 r_T V_T \quad (25)$$

The heat required to raise the temperature of the water from the mesophilic level ($T_M$°C.) to the thermophilic level ($T_T$°C.) is $$H_{TD} = (1-c)bF(T_T - T_M)4.19 \times 10^3 \quad (26)$$

Illustrative Calculation
Given:
$x_\omega = 3$ kgm$^{-3}$; g=15; b=1/14; $Y_c$=0.4;
$B_o$ of sewage feed=0.25 kg$O_2$m$^{-3}$
$Y_{o/s}$=0.534; d=0.333; F=256 m$^3$h$^{-1}$; $t_{rm}$=5 h;
$r_T$=1.60 kg$O_2$m$^{-3}$h$^{-1}$; $T_M$=20° C.; $T_T$=80° C.
Calculated:
$S_r$=0.468 kg m$^{-3}$
C=0.931; $S_\alpha$=0.520 gl$^{-1}$; $x_\alpha$=2.793 gl$^{-1}$;
$S_\beta$=33.8 gl$^{-1}$; $x_\beta$=4.50 gl$^{-1}$; $X_\gamma$=18.0 gl$^{-1}$;
$F_M$=274.3 m$^3$ h$^{-1}$; $V_M$=1371.5 m$^3$; $F_T$=1.68 m$^3$h$^{-1}$;
$V_T$=19.0 m$^3$; $t_{rT}$=11.3 h; $r_{md}$=0.0557 kg$O_2$m$^{-3}$h$^{-1}$;
$H_T$=437×10$^3$ kJh$^{-1}$; $H_{TD}$=317 kJh$^{-1}$. Assuming half of $H_{TD}$ can be recycled by the heat exchanger, the surplus heat production in the thermophilic digestor is, $H_S$=(437−0.5×317)×10$^3$=278.5×10$^3$ kJh$^{-1}$=77.4 kW.

Four Stage Biocombustion

Figure 5:
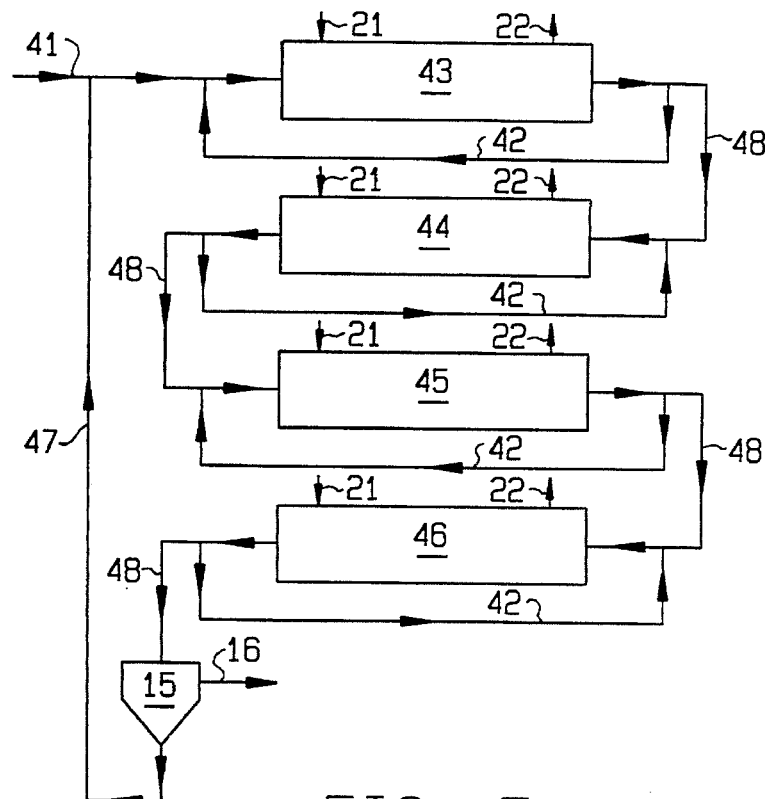
FIGS. 5–7 show a 4-stage system.

The four-stage biocycle depicted in FIG. 5 contains four aerated plug flow reactors 43, 44, 45 and 46, a suitable design for which is described in our co-pending UK Patent Application No. 9209175.0, filed 28 Apr. 1992, the contents of which are included herein by reference. The first reactor 43 is a thermophilic (T) stage, the second 44 is mesophilic (M), the third 45 is thermophilic and the fourth 46 is mesophilic. Each plug flow reactor is provided with a 'stage recycle' 42 which provides the microbial inoculum required at the beginning of the stage, whilst the rest of the outflow from the reactor constitutes the 'passage stream' 48 going into the next stage in the cycle. The passage stream 48 from the fourth reactor 46 passes into a settler or other form of sedimentation device which concentrates the final suspended solids consisting of active biomass, and clarifies the supernatant liquor. The cycle is completed by recycling all of the sedimented solids by stream 47 to the inlet of the first reactor 43. Clarified supernatant deprived of organic matter, leaves the settler in stream 16. The biocycle depicted in FIG. 5 is said to consist of two T-M (thermophilic-mesophilic) sequences linked into a cycle.

Fresh substrate, for instance, sewage sludge, is fed into the biocycle through stream 41. The fresh substrate together with mesophilic biomass from the fourth stage 46 forms the substrate for thermophilic microbial digestion and growth in the first stage 43; the biomass produced in reactor 43 is the substrate for mesophilic digestion in reactor 44; the biomass produced in reactor 44 is the substrate for the thermophiles in reactor 45, and the biomass from reactor 45 is the substrate for the mesophilic reactor 46.

Air or oxygen for aeration of the culture is supplied to each reactor through inlet 21, and effluent gas leaves through outlet 22. The rate of the biocombustion is limited by the maximum oxygen transfer rate ($r_{max}$, kg $O_2$ m$^{-3}$h$^{-1}$) which the aeration system can achieve. Other possible causes of biocombustion rate limitation are insufficient sludge substrate, or insufficient biomass feedback in the stage recycle. The residence time (h) in each stage is given by, $t_r = V_r/F_r$ wherein $V_r$(m³) is the stage liquid volume and $F_r$(m³h⁻¹) is the liquid flow rate through the reactor. In the oxygen-limited process, the minimum residence time for a stage will be $\Delta s_o/r_{max}$(h) where $\Delta s_o$ is the COD (chemical oxygen demand, kg O₂) in that stage. The desired residence time may be achieved by adjusting the reactor volume. The residence time allowed for sewage sludge biocombustion may exceed the minimum time, if convenient.

Each stage develops its own particular microbial population adapted to its particular substrate and maintained by means of the stage recycle. In domestic sewage sludge digestion the thermophilic populations (at 77°–80° C.) consist predominantly of bacterial gram positive rods; however same gram negative rods are found, particularly in the second thermophilic stage 45. The mesophilic populations present in reactors 44 and 45 consist predominantly of bacterial gram negative rods.

In the settler, the suspended solids obtained from biocombustion of sewage sludge, flocculate and settle rapidly. The SVI (sludge volume index) value becomes less than 50 ml/gDM in thirty minutes. If the sludge volume in the settler is excessive, it can be reduced either by decreasing the amount of fresh sludge fed into the system through stream 41, or by increasing the number of T-M sequences in the biocycle. Conversely the number of T-M sequences may be reduced if the sedimented sludge volume is small enough.

The settler may be eliminated if there is no need to remove water from the system, and it is sufficient to charge the reactors initially with liquid medium. This is possible if a dry substrate such as straw is fed to the biocycle. Also evaporation from the biocycle by aeration, possibly enhanced by reducing the pressure to achieve boiling, may be sufficient to keep the volume constant. If mineral matter is present in the feed, dilution of the reactor contents with water either occasionally or continuously and use of a solids separator to recycle the suspended solids and remove some of the minerals in the effluent liquid may be essential. If an excessive amount of minerals becomes attached to the sludge it may be removed by bleeding off a fraction of the sludge, then stripping off the mineral matter by shear, for instance, in a hydrocyclone, or by chemical treatment such as washing with dilute nitric acid or a solution of a metal chelating agent, after which the sludge may be recycled to the first stage of the biocycle.

The biocycle is represented as a continuous plug flow process in FIG. 5. However, it is possible to replace each plug flow stage by a batch culture with the same inoculum size and a culture duration equal to the liquid residence time ($t_r$) in the plug flow reactor. At the end of each batch culture, a fraction (1–j) is passaged to the next culture in the cycle, leaving a fraction j as the inoculum for the succeeding culture. Finally the passaged fraction (1–j) from the last batch culture in the cycle is transferred to a settler so that the suspended solids can be separated and recycled to the first batch culture, which is also fed with the fresh substrate. Assuming the interruption of the batch cultures by the passages does not have any side effects, the result should be the same as that of the biocyle with plug flow cultures.

Figure 7:
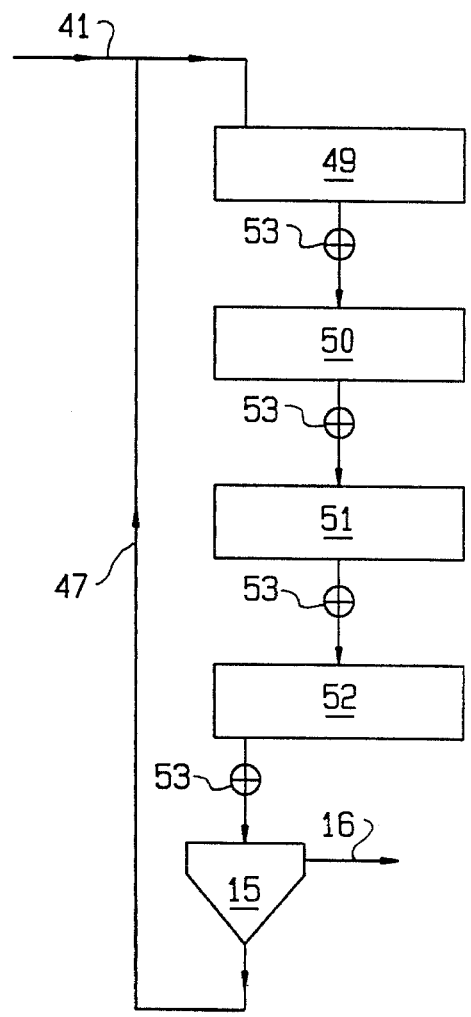

FIG. 7 depicts a biocycle consisting of four batch cultures in which waste matter, for example fresh sludge, is introduced to the first culture stage 49, and stopcock 53 is opened at the end of each of stages 49–52 to passage culture to the next stage, leaving behind 10% of culture volume as inoculum for the next stage. Outflow from the final stage passes to a settler 15 from which clarified supernatant is withdrawn via stream 16, and suspended solids concentrated in the settler are returned to the first stage.

The biocycle with batch culture stages is useful to dispose of relatively small quantities of substrate, or when the type of bioreactor or waste material available does not lend itself to plug flow culture.

The aerobic biocycle can be applied to biocombustion of any organic matter which is biodegradable. The biocycle is particularly advantageous for the disposal of wastewater sludges, because it makes dewatering unnecessary, it kills all known pathogens when the thermophilic temperature is 65° C. or higher, and it can be operated efficiently in small decentralized plants, as well as in large centralized plants. Other substrates of importance are: agricultural crop residues, farm animal wastes and municipal solid wastes. Solid wastes such as straw or paper need to be milled into fine powders or suspensions in order to increase the biocombustion rate.

The multiple T-M sequence biocycle such as the double T-M sequence type illustrated in FIG. 5, can also under anaerobic conditions achieve total biomethanation of organic matter, that is, without net biomass formation.

It may be possible to substitute completely mixed, chemostat type, continuous cultures in place of the plug flow cultures shown in FIG. 5, which substitution would also make the stage recycles 42 unnecessary. The cycle would be completed by recycle of the sedimented solids from the last stage in the process recycle 47.

Mathematical Model of Four Stage Biocycle

Notation and Units $A_F$=(1–b–j), ratio of sludge feed rate ($F_0$) to liquid flow rate through reactor ($F_r$), dimensionless
b=(1/g), process recycle fraction, dimensionless
g=solids concentration factor in settler, dimensionless
$F_0$=sewage sludge flow rate into biocycle, m³h⁻¹
$F_r$=liquid flow rate through reactor, m³h⁻¹
j=stage recycle fraction, dimensionless
r=oxygen transfer rate, kg O₂m⁻³h⁻¹; subscript max indicates maximum value
s=concentration of volatile suspended solids (VS), kg m⁻³; $s_1$ and $s_2$, initial and final values in reactor 43; $s_3$ and $s_4$, initial and final values in reactor 44; $s_5$ and $s_6$, initial and final values in reactor 45; $s_7$ and $s_8$ initial and final values in reactor 46.
$s_r$=concentration of volatile suspended solids (VS) in sludge feed, kg m⁻³
$V_r$=liquid volume in reactor, m³

Figure 6:
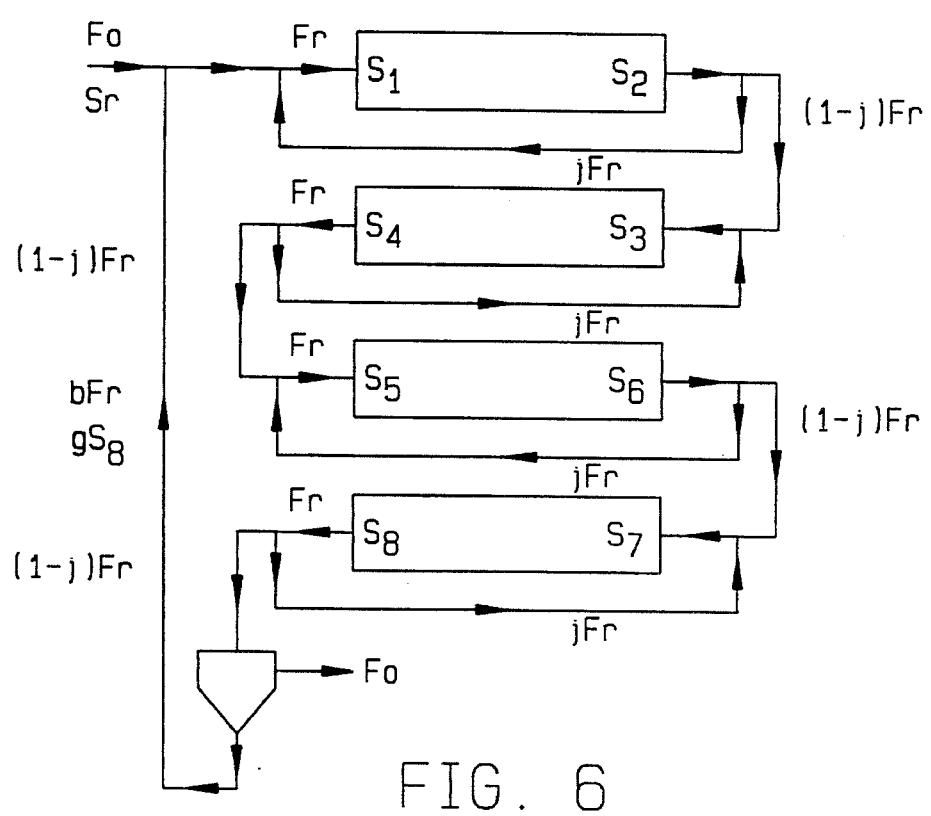

We make the simplifying assumption that all of the substrate is present as suspended solid particles and that the dissolved substrate is negligible. The values of the various parameters at different points in the biocycle are shown in FIG. 6.

From the liquid balance on the first stage (reactor 43) we obtain $$F_r = F_o + bF_r + jF_r \tag{27}$$

hence, $$F_r = F_o/A_F \tag{28}$$

where $$A_F = 1 - b - j.$$

The VS concentrations in the reactors, $s_1$ $s_2$ etc. are the sums of the substrate solids and the active biomass solids. The VS input into the first stage ($F_rS_1$) is the sum of the sewage sludge feed ($F_oS_r$), the process recycle ($bF_rgs_8=F_rS_8$) and the stage recycle, $jF_rS_2$, that is, $$F_rS_1=F_oS_r+F_rS_8+jF_rS_2 \tag{29}$$

It is assumed that the residence time in the stage is long enough to ensure the digestion of all the initial substrate so that $s_2$ represents the final active biomass concentration and the initial active biomass concentration is $js_2$. From Equation 29 we derive, $$S_1=A_FS_r+S_8+jS_2 \tag{30}$$

The VS input rate into the second stage reactor 44 ($F_rS_3$) is given by the sum of the inputs from the first stage $(1-j)$ $F_rS_2$ and the stage recycle ($jF_rS_4$), that is, $$F_rS_3=(1-j)F_rS_2+jF_rS_4 \tag{31}$$

hence $$S_3=(1-j)S_2+jS_4 \tag{32}$$

similarly we derive, $$S_5=(1-j)S_4+jS_6 \tag{33}$$

$$S_7=(1-j)S_6+jS_8 \tag{34}$$

It is assumed that the process is oxygen limited, and that $COD=1.3 \times VS$. Then the minimum residence time required in each stage will be $1.3 \times \Delta S/r_{max}$ where $\Delta s$ is the decrease in the VS in the stage.

Single Vessel Biocycle

A biocycle may also be operated in a single vessel by changing the conditions, in particular, the temperature and inoculum, successively. Thus a culture vessel is charged with fresh sewage sludge, the temperature is adjusted to the thermophilic level, adapted first-stage inoculum, about 10% of the total volume, is added and the culture is aerobically operated for the required duration of the first stage. Then the culture temperature is decreased to the mesophilic level, second-stage, mesophilic, adapted inoculum is added and the culture is operated for the required duration of the second stage. Similarly the culture is taken through the third, thermophilic, and fourth, mesophilic, stages. After the fourth stage, the culture is allowed to settle, clarified supernatant is removed and the sedimented solids are retained in the vessel; more sewage sludge is added to bring the volume up to say 90% of the total required, the temperature is increased to the thermophilic level and new first-stage thermophilic inoculum (10% of the total volume) is added to start the next cycle.

If desired, a proportion of the culture may be withdrawn from each stage to make room for the inoculum to be added and the withdrawn material may be used as substrate for the seed culture providing the inoculum for the next stage of the same type.

This method has the advantage that it permits the duration of each stage to be varied at will, and thereby optimized. Another advantage is that the provision of pumps to passage the culture from stage to stage can be eliminated with consequent economies.

A single vessel biocycle is of special interest in organic waste disposal and reduction of sludge volume to zero by total biomethanation because biomethanation processes take much longer than aerobic biocombustion, thus any transient disturbance caused by adjustment of temperature or other condition between stages is made less important. The concentrated nature of piggery waste or other manures may require more than two T-M sequences to achieve sufficient separation of clarified supernatant at the end of the last stage.

In contrast to the biocycle of the present invention, conventional biomethanation can reduce sludge organic matter by about one half only, and the sludge volume remains virtually unaltered.

Figure 8:
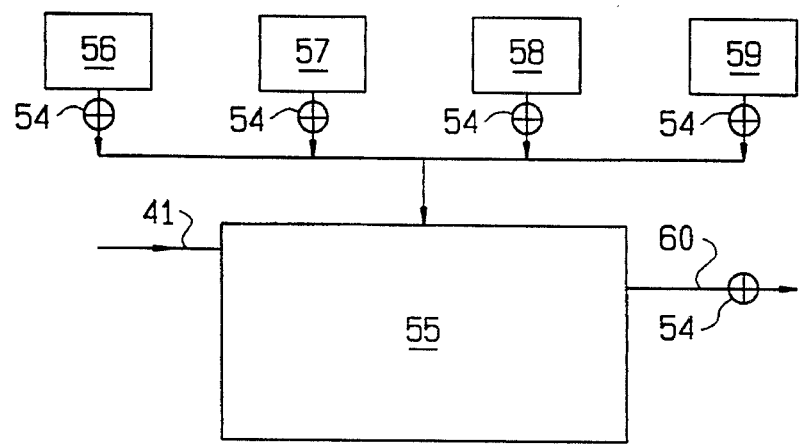
FIG. 8 shows a single vessel system.

A schematic version of a single vessel biocycle as depicted in FIG. 8 in which seed (inoculum) cultures are maintained in tanks 56–59 and portions are passed to the single culture vessel 55 at appropriate stages of the cycle by means of stopcocks 54. Fresh sewage sludge enters the culture vessel by Stream 41. The vessel may also act as a settler, to sediment suspended solids at the end of the last stage in the cycle and after the final stage, supernatant may be withdrawn from outlet 60.

The following Examples are given by way of illustration only.

EXAMPLE 1

Cyclic 2-stage system

A cyclic two-stage system is used to oxidize completely domestic sewage and avoid net production of sludge. The system, as shown in FIG. 1, consists of a mesophilic plug flow fermentor 11, of the type shown in FIG. 1 of our co-pending International Patent Application No. PCT/EP91/01323 filed on 12 Jul. 1991, the contents of which are incorporated by reference, and a thermophilic plug flow fermentor 12 of similar type to fermentor 11. Each stage is aerobic. Sewage with a B.O.D. of 250 $mgl^{-1}$ is fed (stream 13) into the mesophilic stage at a rate of 256 $m^3h^{-1}$ and combined with the effluent stream 20 from the thermophilic digestor. The volume of the mesophilic stage is 1,372 $m^3$ and the liquid residence time is 5 h. This stage may consist of a number of fermentor modules (vessels) operated in parallel. The fermentor is aerated to provide the necessary oxygen uptake rate of 1.74 $molm^{-3}h^{-1}$. The effluent from the mesophilic stage, stream 35 with a sludge concentration of 3 kg VSS passes to the separator 15 which may be common to all the mesophilic fermentor modules. The separator concentrates the sludge from 3 to 45 g VSS $m^{-3}$. The clarified liquor exits in stream 16 at a flow rate of 256 $m^3h^{-1}$. Part of the concentrated sludge is fed back through stream 14 at a flow rate of 17 $m^3h^{-1}$. The excess sludge (1.26 $m^3h^{-1}$) is fed via stream 18 to the thermophilic stage 12 which has a volume of 19.0 $m^3$. This stage is maintained, by self-heating, at 80° C. The oxidation rate in the thermophilic stage is limited by the oxygen transfer rate which is set at 50 mol $m^{-3}$ $h^{-1}$. Part of the culture effluent from the thermophilic stage (0.42 $m^3$ $h^{-1}$) is fed back through stream 19 to act as inoculum. The rest of the thermophilic culture (1.26 $m^3$ $h^{-1}$) is returned via stream 20 to the inlet of the mesophilic stage, in which the thermophilic sludge is digested.

The inoculum for the mesophilic stage is provided by activated sludge from a conventional sewage purification plant. The inoculum for the thermophilic stage is developed from a composted manure heap at a high temperature in the thermophilic range. About 100 g of the compost is mixed with activated sludge (about 50 g VSS) and water 1000 ml is aerated in a bottle or shake flask incubated at 80° C. for 5 days or more. The culture is scaled up by doubling the amount of sludge and water roughly every 5 days. The pH is about 7.5.

The surplus heat output of the thermophilic stage, about 77 KW, may be recovered from the coolant or exit vapour at a useful temperature, near 80° C.

EXAMPLE 2

Four-stage Biocycle

By way of example, a description is given below, of a biocycle with four stages, in two T-M sequences, for the biocumbustion of sewage sludge. The notation used follows that given in the accompanying mathematical model. The sludge substrate was obtained from treatment of domestic sewage at a London sewage works. It was stored as centrifuged 'sludge cake' at 4° C. and reconstituted in water when required.

The inocula for the thermophilic stages were originally derived from horse manure compost in its thermophilic phase. The inocula for the mesophilic stages were derived from domestic sewage sludge. These inocula were adpated to their particular substrates by numerous subcultures at the process temperatures.

The biocycle consisted of four batch cultures arranged in two T-M sequences, first stage (T1) at 77° C.; second stage (M1) at 37° C.; third stage (T2) at 77° C.; fourth stage (M2) at 37° C. Drechsel bottles (250 ml capacity) were used for the thermophilic stages held in a water bath at 77° C. Shake flasks (250 ml capacity) incubated on an orbital shaker at 150 rpm were used as the mesophilic stages. Each culture had an initial volume of 100 ml. The Drechsel bottles were aerated by humidified air supplied through the sparger at 30–40 ml min$^{-1}$. Slight evaporation occurred in the cultures (2% per day at 77°, less at 37°). At the end of the stage, the final volume was restored to 100 ml by the addition of de-ionized water. At the end of a stage the cultures were passaged to the next stage. This was done by transferring 90 ml (fraction (l–j)=0.9) from the fourth (final) stage to a settler (a 100 ml measuring cylinder) leaving 10 ml (fraction j=0.1) of culture as inoculum for the following stage. From each of the preceding cultures 90 ml was passaged to the next stage leaving 10 ml as inoculum for the next culture. The suspended solids in the settler readily sedimented to form a flocculent precipitate with an SVI (sludge volume index) of 40 ml g$^{-1}$ DM at 30 min. An aliquot, 40 ml ($A_F$=0.4) of the clarified supernatant was removed, and the remaining suspended solids concentrated in 50 ml (g=2) were recycled to the first stage. Reconstituted sludge (40 ml) was added to the first stage to restore its volume to 100 ml and provide the substrate input. Having completed the passages, the cultures were re-incubated.

The final supernant, removed from the culture, was pale brown in colour and slightly turbid. On standing the supernatant for a few hours, the residual suspended solids precipitated and the supernatant was practically clarified.

The vapours from the various stages had a slight but not obnoxious odour.

The biocycle reached a steady state in two cycles (8 stage passages) in that the sludge volumes in each stage, after settling showed no upward or downward trend. The inputs and outputs of materials to and from the four stages of the biocycle after 3.75 cycles are shown in Table 1.

The first part of the table shows that the biocycle eliminated by biocombustion 97% of the sludge volatile matter supplied. This means that a biocycle with a combined reactor volume of 4 m$^3$, would dispose of 1.6 m$^3$ (about 1.6 tonnes) of liquid sewage sludge per cycle.

TABLE 1

Biocombustion of sewage sludge volatile matter (VM) in a four stage* (2 T-M sequences) biocycle

| Material | Sewage sludge inputs per cycle | Supernatant outputs per cycle | Decrease per cycle * |
|---|---|---|---|
| Water (m$^3$) | 1.60 | 1.60 | 100 |
| Dry matter (kg) | 27.9 | 1.07 | 96 |
| Volatile matter (kg) | 23.3 | 0.62 | 97 |

*Volume of each stage, 1 m$^3$
Suspended solids present at end of stage and consumption of materials in each stage

| Stage | Dry matter in suspended solids (kg m$^{-3}$) | Volatile matter in suspended solids (kg m$^{-3}$) | Consumption of total volatile matter in each stage+ (%) |
|---|---|---|---|
| Thermophilic 1 (T1) | 13.7 | 10.0 | 52 |
| Mesophilic 1 (M1) | 13.0 | 9.6 | 17 |
| Thermophilic 2 (T2) | 10.5 | 7.8 | 27 |
| Mesophilic 2 (M2) | 10.0 | 7.2 | 5 |

+sum of suspended solids and dissolved matter in supernatant

The residual 3% of the VM dissolved in the supernatant at a concentration of 390 ppm may be readily polished off by conventional activated sludge treatment.

Within experimental error all of the DM and VM were accounted for. About 10% of the input of ash material emerged in the effluent supernatant. The ash content of the dry matter in the suspended solids reached 25 to 28% in the steady state compared with 17% in the DM of the sludge.

On the assumptions that the COD of the sludge is 1.3× VM, and $r_{max}$, 1 kg O$_2$ m$^{-3}$h$^{-1}$, then the biocycle described in this example, with a sludge COD feed rate of 30.3 kg per cycle, requires a minimum cycle time of 30.3 h, with 15.7, 5.1, 8.1 and 1.4 h respectively in the T1, M1, T2 and M2 stages. In this illustrative example the minimum cycle time was arbitrarily set at 4 days with passages from stage to stage daily.

I claim:

1. A method of degradation of organic matter, wherein said organic matter in aqueous suspension and/or solution is subjected alternately to a cycle which includes a thermophilic digestion stage at 60° to 105° C. and a mesophilic digestion stage at 10° to 50° C., said cycle comprising at least four stages, including at least two of said thermophilic stages and two of said mesophilic stages, commencing with a thermophilic stage and ending with a mesophilic stage, said cycle including recycling of solid matter from the final mesophilic stage to the first thermophilic stage with input of fresh organic matter, whereby in the mesophilic stage said organic matter and any thermophilic microorganisms present are at least partly digested, and whereby in said thermophilic stage said organic matter and any mesophilic microorganisms present are at least partly digested, and whereby said organic matter is substantially completely converted into gaseous degradation products.

2. A method as claimed in claim 1 wherein in the mesophilic stage any thermophilic microorganisms are inactivated and in the thermophilic stage any mesophilic microorganisms are inactivated, said inactivation being effected by means of the shift in temperature.

3. A method as claimed in claim 1 or claim 2 wherein the digestion stages are carried out in fermentor tanks and wherein means are provided for passing the material between the said tanks..

4. A method as claimed in claim 3 wherein the separate stages are carried out in separate tanks.

5. A method as claimed in claim 3 wherein at the end of the cycle, the material is passed to a sedimentation device and the suspended solids thereby collected are passed to the first digestion stage of initiation of a further cycle with fresh organic matter.

6. A method as claimed claim 3 wherein each stage is operated in plug flow mode, with recycling of at least part of the material within each individual stage.

7. A method as claimed claim 3 wherein each stage is operated in batch mode and where the culture contents from each stage are partially passaged to the next stage retaining a fraction to form an inoculum for the next culture of that type in the cycle.

8. A method as claimed in claim 1 wherein said method is carried out in a single reaction vessel in which the temperature is successively altered, and appropriate microorganisms added as an inoculum for each of the separate stages and where at the end of the cycle the supernatant is removed and fresh organic matter added to the remaining solids to initiate the next degradation cycle.

9. A method as claimed in claim 1 wherein the cycle comprises 4 stages, each operated in the form of a completely mixed chemostat type continuous culture.

10. A method as claimed claim 3 operated in aerobic fashion.

11. A method as claimed in claim 3 wherein said organic matter is wastewater sludge, agricultural crop residues, farm animal wastes, industrial wastes, municipal and solid waste, sewage sludge or biodegradable plastic waste.

12. A method as claimed in claim 3 wherein the temperature shift between the two stages is at least 20° C.

13. A method as claimed in claim 3, wherein one cycle of said method comprises two mesophilic stages, alternating with two thermophilic stages.

14. A method for degrading organic material in an aqueous solution or suspension, which comprises:

subjecting the solution or suspension to a cycle of at least two thermophilic digestion stages, operating at a temperature of about 60° to 105° C., and at least two mesophilic digestion stages, operating at about 10° to 50° C., commencing with a thermophilic stage and ending with a mesophilic stage, whereby in the mesophilic stage the organic matter and any thermophilic microorganisms present are at least partly digested, and whereby in the thermophilic stage the organic matter and any mesophilic microorganisms present are at least partly digested; and recycling solid matter from the final mesophilic stage of the cycle to the first thermophilic stage of the cycle to substantially completely convert the organic material to gaseous degradation products.

15. A method as claimed in claim 13 wherein the separate stages are carried out in separate tanks.

16. A method as claimed in claim 13 which further comprises collecting suspended solids from the solution or suspension at the end of the cycle, and directing the solids along with a solution or suspension of fresh organic matter to the first thermophilic digestion stage.

17. A method as claimed claim 13, wherein each stage is conducted in a separate reaction vessel, under aerobic conditions.

18. A method as claimed in claim 13, wherein the temperature shift between the two stages is at least 20° C.

* * * * *